US011051703B2

(12) United States Patent
Liu et al.

(10) Patent No.: US 11,051,703 B2
(45) Date of Patent: Jul. 6, 2021

(54) METHOD AND DEVICE FOR DETECTING A VITAL SIGN CARRYING SIGNAL USING A PHASE-LOCKED LOOP

(71) Applicant: Stichting IMEC Nederland, Eindhoven (NL)

(72) Inventors: Yao-Hong Liu, Eindhoven (NL); Marco Mercuri, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 327 days.

(21) Appl. No.: 15/894,729

(22) Filed: Feb. 12, 2018

(65) Prior Publication Data

US 2018/0235481 A1 Aug. 23, 2018

(30) Foreign Application Priority Data

Feb. 13, 2017 (EP) .................................. 17155844

(51) Int. Cl.
*A61B 5/0205* (2006.01)
*G01S 13/58* (2006.01)
(Continued)

(52) U.S. Cl.
CPC .......... *A61B 5/0205* (2013.01); *A61B 5/0507* (2013.01); *A61B 5/1135* (2013.01); *G01S 13/583* (2013.01); *G01S 13/88* (2013.01)

(58) Field of Classification Search
CPC ... A61B 5/0205; A61B 5/1135; A61B 5/0507; G01S 13/583; G01S 13/88
See application file for complete search history.

(56) References Cited

U.S. PATENT DOCUMENTS

| 2012/0235689 A1* | 9/2012 | Jau ........................ G01S 13/583 |
| | | 324/629 |
| 2014/0270002 A1* | 9/2014 | Schubert ............... H04L 1/0045 |
| | | 375/320 |
| 2016/0022154 A1* | 1/2016 | Warnking ............. A61B 5/6851 |
| | | 600/486 |

OTHER PUBLICATIONS

"Intermediate frequency," Wikipedia. Captured from Nov. 7, 2016 using Wayback Machine. (Year: 2016).*
(Continued)

*Primary Examiner* — Serkan Akar
*Assistant Examiner* — Richmond J Van Winter
(74) *Attorney, Agent, or Firm* — Knobbe, Martens, Olson & Bear, LLP

(57) ABSTRACT

A method of detecting a vital sign comprising at least one of a heart rate and a respiratory rate of a subject is provided. In one aspect, the method includes transmitting a radio frequency signal towards the subject; and receiving a reflected signal from the subject, wherein the transmitted signal is reflected by the subject and Doppler-shifted due to at least one of the heart rate and the respiratory rate to form the reflected signal. The method also includes mixing the reflected signal with a first reference signal; and providing a vital sign carrying signal based on the mixing to a first input of a phase or frequency comparator. The method further includes generating an adjustable second reference signal and providing the reference signal to a second input of the phase or frequency comparator; and generating an output signal, by the phase or frequency comparator. The method includes varying at least one of a phase and a frequency of the adjustable second reference signal based on the output signal to track a phase or frequency of the vital sign carrying signal.

19 Claims, 9 Drawing Sheets

(51) Int. Cl.
A61B 5/113 (2006.01)
A61B 5/0507 (2021.01)
G01S 13/88 (2006.01)

(56) References Cited

OTHER PUBLICATIONS

XIA et al., Dual-Carrier Noncontact Vital Sign Detection With a Noise Suppression Scheme Based on Phase-Locked Loop, IEEE Transactions on Microwave Theory and Techniques, vol. 64, No. 11, Nov. 2016. (Year: 2016).*

Extended European Search Report, dated Aug. 22, 2017 in European Application No. 17155844.8.

Gu et al., Instrument-Based Noncontact Doppler Radar Vital Sign Detection System Using Heterodyne Digital Quadrature Demodulation Architecture, IEEE Transactions on Instrumentation and Measurement, vol. 59, No. 6, Jun. 2010.

Wu et al., Phase- and Self-Injection-Locked Radar for Detecting Vital Signs with Efficient Elimination of DC Offsets and Null Points, IEEE Transactions on Microwave Theory and Techniques, vol. 61, No. 1, Jan. 2013.

Xia et al., Dual-Carrier Noncontact Vital Sign Detection With a Noise Suppression Scheme Based on Phase-Locked Loop, IEEE Transactions on Microwave Theory and Techniques, vol. 64, No. 11, Nov. 2016.

Xiao et al., Frequency-Tuning Technique for Remote Detection of Heartbeat and Respiration Using Low-Power Double-Sideband Transmission in the Ka-Band, IEEE Transactions on Microwave Theory and Techniques, vol. 54, No. 5, May 2006.

* cited by examiner

METHOD AND DEVICE FOR DETECTING A VITAL SIGN CARRYING SIGNAL USING A PHASE-LOCKED LOOP

CROSS-REFERENCE TO RELATED APPLICATIONS

This application claims foreign priority to European Patent Application No. 17155844.8, filed Feb. 13, 2017, the contents of which are incorporated by reference herein in its entirety.

BACKGROUND

Technological Field

The present disclosure relates to a method for detecting a vital sign including at least one of a heart rate and a respiratory rate of a subject. The present disclosure also relates to a device for detecting the vital sign.

Description of the Related Technology

In recent years, contactless vital signs monitoring has been an increasingly active field of research. The sensing of vital signs can be made contactless and therefore non-invasive by adopting radar techniques. The Doppler shifts caused by the mechanical movements of the heart and the lungs can be detected and analyzed to determine the heart rate and the respiration rate.

A continuous-wave (CW) radar, also known as a Doppler radar, transmits a radio frequency single-tone continuous-wave signal which is reflected by a target and then demodulated in a receiver. By the Doppler effect, the radio frequency signal reflected by the moving tissue of the target undergoes a frequency shift proportional to the surface velocity of the tissue. If the moving tissue has a periodic motion (as the tissue in the chest region of a subject may have due to the period motion of the heart and the lungs) the Doppler effect results in a phase shift of the reflected radio frequency signal which is proportional to the instantaneous surface displacement. In the receiver, the transmitted signal may be mixed with the reflected Doppler-shifted signal to produce a mixing product which, following low pass filtering, results in a baseband signal including a low frequency component that is directly proportional to the instantaneous surface displacement.

However, extraction of the low frequency component from the baseband signal in the Doppler radar-based approach requires that the maximum amplitudes of the chest region displacements due to the heart beat and the respiration are much smaller than the wavelength of the radio frequency signal. This may be referred to as the small angle approximation. Assuming, for a typical subject, an average maximum amplitude of the chest tissue displacements due to the heart beat and the respiration of about 0.08 mm and 0.8 mm, respectively, this condition may be easily satisfied by, for example, using a radio frequency signal with $\lambda=0.125$ m (2.4 GHz), yielding a maximum phase shift of approximately 5 degrees. In such conditions, the baseband signal may still include some non-linear terms (such as inter-modulation products between the heart rate and the respiration rate) but the terms which are linearly proportional to the instantaneous tissue displacement due to the heart rate and the respiration rate will tend to dominate. However, a tissue displacement of merely 8 mm will produce a phase shift of about 46 degrees and violate the small angle approximation. This implies that in case of random movements of the subject causing a random displacement of the reflecting tissue, reliable extraction of the heartbeat and respiration rates from the baseband signal is severely hampered.

A further condition for extraction of the low frequency component from the baseband signal in the Doppler radar-based approach is that the fixed phase offset between the transmitted signal and the reflected signal (i.e., the part of the phase shift not being due to the Doppler-shift, such as the mean distance between the radar and the subject, the reflection at the subject, and radio block delay) is an odd multiple of $\pi/2$. This may be referred to as the optimum operation point (or the "optimum point") of the Doppler radar. Unless this condition is met, a mathematical analysis of the mixing product reveals that the baseband signal will be distorted by non-linear terms doubling and mixing the frequency components corresponding to the heart rate and the respiration rate. Furthermore, frequency components corresponding to the heart rate and the respiration rate will be multiplied by the total residual phase noise between the transmitter and the receiver, thereby degrading the signal-to-noise ratio. This issue will be particularly pronounced when the fixed phase offset between the transmitted signal and the reflected signal is an integer multiple of $\pi$. This may be referred to as the null operation point (or the "null point") of the Doppler radar.

The null points and the optimum points are distributed alternately and are separated by $\lambda/8$, where $\lambda$ represents the wavelength of the transmitted signal. At the commonly used operating radio frequencies, the distance between an adjacent null point and optimum point is in the order of few millimeters or centimeters. For example, at 2.4 GHz this distance is about 1.5 cm. Therefore, obtaining a reliable measurement at the optimum point is in practice very difficult to achieve. Meanwhile, reducing the operating frequency will increase null point-optimum point separation but also will decrease the sensitivity in detecting the vital signs parameters.

Ping-Hsun Wu et al. proposes in "Phase- and Self-Injection-Locked Radar for Detecting Vital Signs with Efficient Elimination of DC Offsets and Null Points" (IEEE Transactions on Microwave Theory and Techniques, Vol. 61, No. 1, pp. 685-695, January 2013) an alternative Doppler radar system for vital signs monitoring which employs a phase- and self-injection-locked (PSIL) oscillator. A fine tuning voltage for a dual-tuning voltage-controlled oscillator (VCO) is controlled by a phase-locked loop (PLL) to extract the Doppler-shifted signal. The output signal of the VCO is fed to both the transmitting antenna and a phase frequency detector (PFD) of the PLL. The received Doppler-shifted signal is injected into the VCO through a circulator to form an SIL loop. The SIL loop is phase-locked by the PLL to stabilize the output frequency. A Doppler-shifted injection signal will result in an output phase perturbation of the VCO. The phase perturbation is detected by the PFD comparing the Doppler-shifted injection signal to an output signal of a fixed frequency reference oscillator. A charge pump (CP) circuit and a loop filter transform the output of the PFD into a fine tuning voltage for tuning the intrinsic oscillation frequency of the VCO. Provided that the maximum amplitude of the displacement of the target is much smaller than the free-space wavelength of the transmitted signal, the VCO fine tuning voltage controlled by the PLL reflects the phase variation of the Doppler signal due to the heartbeat. Hence, this architecture also relies on the small angle approximation. Furthermore, the PSIL radar exhibits "null points" since there will be points at which there is a zero power spectral SNR gain wherein detection of a displacement is prevented. Therefore, a path diversity switch is employed to periodically switch between two transmission paths presenting a phase difference of $\pi/2$. However, the null point problem may still only be mitigated by the path diversity switch provided that the small angle approximation is valid.

An alternative solution for detection of vital signs is to use a quadrature Doppler radar architecture in combination with an arctangent demodulation technique. Such an approach does not require the small angle approximation condition and it may also avoid the "null point" problem. On the other hand, the vital sign may only be detected if DC information of the target is preserved. However, radio frequency and baseband amplifiers may be required to amplify the weak reflection signal. Thus, the DC information will also be amplified and the receiver may be saturated when the subject approaches the radar antennas. Moreover, any phase and magnitude imbalance between in-phase and quadrature channels will degrade the detection. Changzhan Gu et al. proposes in "Instrument-Based Noncontact Doppler Radar Vital Sign Detection System Using Heterodyne Digital Quadrature Demodulation Architecture" (IEEE Transactions on Instrumentation and Measurement, Vol. 29, No. 6, pp. 1580-1588, June 2010) a digital heterodyne quadrature demodulation architecture that helps mitigate quadrature channel imbalance and eliminate the complicated DC offset calibration for arctangent demodulation. However, in order to properly extract the phase, two channels are required in combination with a phase unwrapping algorithm or a differentiate and crossmultiply algorithm.

SUMMARY OF CERTAIN INVENTIVE ASPECTS

In view of the above, a general objective of the disclosed technology is to enable contactless detection of at least one of a heart rate and a respiratory rate of a subject by means which are substantially insensitive to subject distance and chest wall random movements of the subject and which do not rely on the small angle approximation. Further objects may be understood from the following.

These and other objectives of certain aspects of the disclosed technology are at least partially met by implementations described and claimed herein.

According to a first aspect, there is provided a method of detecting a vital sign comprising at least one of a heart rate and a respiratory rate of a subject, the method including: transmitting a radio frequency signal towards the subject; receiving a reflected signal from the subject, wherein the transmitted signal is reflected by the subject and Doppler-shifted due to at least one of the heart rate and the respiratory rate to form the reflected signal; mixing the reflected signal with a first reference signal; providing a vital sign carrying signal based on the mixing of the reflected signal with the first reference signal to a first input of a phase or frequency comparator; generating an adjustable second reference signal by a reference signal generator and providing the reference signal to a second input of the phase or frequency comparator; generating an output signal by the phase or frequency comparator based on the vital sign carrying signal and the second reference signal; and varying, by the reference signal generator, at least one of a phase and a frequency of the adjustable second reference signal based on the output signal of the phase or frequency comparator to track a phase or frequency of the vital sign carrying signal.

By feeding back the output signal of the phase or frequency comparator to the reference signal generator and adjusting at least one of a phase and a frequency of the reference signal output by the reference signal generator, the phase or frequency comparator and the reference signal generator form a phase-locked loop which tracks frequency and phase variations of the reflected signal. Thereby, a demodulated output signal may be provided which represents the time-dependent frequency or phase shift of the reflected signal caused by tissue displacement due to the heart rate and/or the respiratory rate.

The output signal of the phase or frequency comparator may thus be indicative of at least one of the heart rate and the respiratory rate. In particular, the output signal may include a component which oscillates at a frequency corresponding to the heart rate and a component which oscillates at a frequency corresponding to the respiration rate. Signal components indicative of at least one of the heart rate and the respiratory rate may hence be extracted from the reflected signal.

In accordance with the methods of the disclosed technology, neither the small angle approximation nor the avoidance of "null points" are conditions for accurate determination of vital signs, as in the prior art approaches. As a result, the heart rate and/or respiration rate may be determined even in the presence of chest wall random movements of the subject reflecting the transmitted signal. This may be understood by considering that in a steady state of the phase locked loop, the output signal of the phase or frequency comparator is independent of the fixed phase offset between the transmitted signal and the reflected signal (i.e., the part of the phase offset not being due to the Doppler-shift, such as the distance to the subject, the reflection at the subject, and radio block delay). A random step change of the fixed phase shift results in a step change of the phase of the reflected signal at the first input of the phase or frequency comparator. The phase or frequency comparator will accordingly generate an output signal which will control the reference signal generator to track the step change of the phase of the reflected signal and, after a transient period, lock on to the phase of the reflected signal at the first input of the phase or frequency comparator. Effects in the output signal of the phase or frequency comparator due to a (given or changed) fixed phase offset may hence be avoided.

The phase locked loop may hence perform down-conversion of the reflected signal to provide a baseband output signal indicative of a frequency or phase difference between the reflected signal and the adjustable reference signal received at the first and the second input of the phase or frequency comparator, respectively. The difference corresponds to the modulation of the reflected signal induced by tissue movement caused by the heartbeat and respiration of the subject.

The phase and/or frequency of the adjustable reference signal may be adjusted to track a phase of the reflected signal with a predetermined offset. As may be understood by the person skilled in the art the predetermined offset may generally depend on the transfer characteristics of the phase or frequency comparator. Hence the frequency and/or phase of the reference signal may be varied such that the reference signal tracks the phase in a lagging or synchronous manner.

Thanks to the mixing of the received, reflected signal with a first reference signal, a mixed signal is created which may be separately analyzed. Thus, the method allows for processing the mixed signal in several different manners in the phase-locked loop. The phase-locked loop could be implemented in analog domain, but could alternatively be implemented in digital domain or in a digital quadrature architecture.

In particular, implementing the phase-locked loop in digital domain provides a flexibility of the method, as a digital implementation may be easily amended. For instance, parameters of the phase-locked loop may be optimized dynamically in software to adapt the vital sign detection to a type of motion being measured.

Also, implementing the phase-locked loop in digital domain may provide tracking of the phase or frequency while avoiding non-linearities that may otherwise be present in analog components.

The radio frequency signal may be transmitted towards a chest region of the subject. The reflected signal may accordingly be Doppler-shifted due to tissue displacement in the chest region caused by at least one of the heart rate and the respiratory rate. The displaced tissue reflecting the transmitted signal may include anyone, or a combination, of the chest wall, the heart and the lung(s) of the subject.

According to an embodiment, a frequency of the first reference signal is different from a frequency of the transmitted signal. This implies that the mixing of the reflected signal with the first reference signal provides an intermediate frequency which is non-zero. The mixed signal of the intermediate frequency may, for example, after being lowpass filtered, be input to the phase or frequency comparator. The phase or frequency comparator produces new signals at the sum and difference of phases present at the first and second inputs. When the phase-locked loop is locked, one output will be at twice the input frequency (the intermediate frequency) and one output will be proportional to a cosine of the phase difference, wherein the doubled frequency component may be removed by a lowpass loop filter. Thus, if the signal based on mixing of the reflected signal with the first reference signal, which feeds the phase-locked loop structure, would be at a zero intermediate frequency, it would be impossible to separate the sum and difference of the phases in the phase-locked loop and distortions may be generated.

However, if a quadrature architecture is used, the reflected signal can be downconverted in baseband, i.e., to a zero intermediate frequency, as it may be possible to separate the sum and difference of the phases provided by the phase or frequency comparator as an inphase and a quadrature channel may be combined in complex form.

According to an embodiment, a signal output by mixing of the reflected signal with the first reference signal is converted into digital domain. This implies that the phase-locked loop may be implemented in digital domain.

However, as mentioned above, the phase-locked loop may alternatively be implemented in analog domain, whereby no analog-to-digital conversion of the mixed signal may be necessary.

According to an embodiment, the steps of providing a vital sign carrying signal; generating an adjustable second reference signal; generating an output signal by the phase or frequency comparator; and varying, by the reference signal generator, at least one of a phase and a frequency of the adjustable second reference signal are performed in digital domain and the reference signal generator comprises a numerically controlled oscillator. Thus, when the signal output by mixing of the reflected signal with the first reference signal is converted into digital domain, the phase-locked loop may also be implemented in digital domain.

According to an embodiment, the received reflected signal is divided into an inphase and a quadrature component. This may allow handling the reflected signal in a quadrature architecture. The phase of the Doppler-shifted signal may then be extracted in the quadrature architecture without a need of using a phase unwrapping algorithm or a differentiate and crossmultiply algorithm.

According to an embodiment, the vital sign carrying signal is a complex form combination of an inphase and a quadrature component. Thus, a phase-locked loop in digital domain may process a single complex form signal.

According to an embodiment, the transmitted signal is generated by a first phase-locked loop and the first reference signal is generated by a second phase-locked loop, wherein the first phase-locked loop and the second phase-locked loop uses the same reference clock. The use of the same reference clock implies that the transmitter and the receiver make use of the same oscillator, whereby phase noise of the transmitted signal and the first reference signal may be partially correlated and, hence, may insignificantly influence the tracking of the phase or frequency of the vital sign carrying signal.

According to an alternative embodiment, the transmitted signal is generated by mixing a signal from a first oscillator and a second oscillator and the first reference signal is generated by the second oscillator. This implies that a simple set-up may be used for generating the transmitted signal and the first reference signal while maintaining a possibility for phase noise not to influence the tracking of the phase or frequency of the vital sign carrying signal.

The first oscillator may further be used by the reference signal generator in the phase-locked loop so that the first oscillator is both used for generating the transmitted signal and for generating the adjustable second reference signal.

According to an embodiment, the method further comprises determining at least one of a heart rate or a respiratory rate by performing a frequency analysis of a signal based on the output signal of the phase or frequency comparator. Hence, the desired vital sign(s) may be identified from the output signal by appropriate frequency analysis techniques, such as Fast Fourier Transform. The output signal of the phase or frequency comparator may be filtered by a loop filter prior to performing the frequency analysis.

According to an embodiment, a frequency of the vital sign carrying signal is tracked. This enables determining at least one of a heart rate and a respiratory rate.

According to another embodiment, a phase of the vital sign carrying signal is tracked and the method further comprises integrating the output signal from the phase or frequency comparator. By integrating the output signal the signal level of the output signal may be increased, thereby simplifying further analysis. Also, by integrating the output signal the time-varying phase variations of the reflected signal resulting from the heart rate and the respiratory rate may be obtained. The heart rate and/or the respiration rate may thereby be readily identified and interpreted from the integrated signal, since the output signal represents a superposition of the mechanical movements due to the heartbeat and the breath and other movement of the tissue reflecting the transmitted signal. Accordingly, the heart rate and/or respiration rate may be determined by performing a frequency analysis of the integrated output. The output signal of the phase or frequency comparator may be filtered by a loop filter prior to being integrated.

On the basis of the integrated output of the phase or frequency comparator, a magnitude of a tissue motion based on heart or respiratory action of the subject may be estimated by determining an amplitude of a frequency component of the integrated output. Hence, information regarding the magnitude of the mechanical movement of the heart and/or the lungs may be extracted from the reflected signal.

According to an embodiment, the phase or frequency comparator includes a mixer. A mixer provides a simple and cost-effective implementation of a phase or frequency comparator. The mixer may generate an output signal oscillating at the difference frequency between the vital sign carrying signal received at the first input and the adjustable second reference signal received at the second input. The method may further comprise filtering the output signal of the mixer to suppress frequency components above the difference frequency, such as a frequency component at the sum frequency of the vital sign carrying signal and the adjustable reference signal, and optionally higher order inter-modulation products.

According to an embodiment, the reference signal generator includes a voltage controlled oscillator. A voltage controlled oscillator provides a simple and cost-effective implementation of an adjustable reference signal generator.

According to an embodiment, the reference signal generator includes an oscillator and a phase modulator. The phase modulator may vary the phase of the reference signal generated by the oscillator to track the phase of the vital sign carrying signal.

The method may further comprise integrating the output signal of the phase or frequency comparator and providing the integrated output signal to the phase modulator. The phase of the adjustable reference signal may hence be varied based on the integrated output signal to track a phase of the vital sign carrying signal.

According to an embodiment, the radio frequency signal transmitted towards the subject is a fixed-frequency signal. This may simplify the hardware implementations of the transmitter- and the receiver-side. In particular the radio frequency signal transmitted towards the subject may be a continuous wave radio frequency signal of a fixed frequency.

According to a second aspect, there is provided a device for detecting a vital sign including at least one of a heart rate and a respiratory rate of a subject, the device including: a transmitter arranged to transmit a radio frequency signal towards the subject; a receiver arranged to receive a reflected signal from the subject, wherein the transmitted signal is reflected by the subject and Doppler-shifted due to at least one of the heart rate and the respiratory rate to form the reflected signal; a mixer for mixing the reflected signal with a first reference signal; and a signal processing circuitry comprising a phase or frequency comparator and a reference signal generator; wherein the phase or frequency comparator is arranged to receive a vital sign carrying signal based on the mixing of the reflected signal with the first reference signal on a first input and receive an adjustable second reference signal from the reference signal generator on a second input of the phase or frequency comparator and to generate an output signal based on the vital sign carrying signal and the second reference signal; and wherein the reference signal generator is arranged to vary at least one of a phase and a frequency of the adjustable second reference signal based on the output signal of the phase or frequency comparator to track a phase or frequency of the vital sign carrying signal.

Effects and features of this second aspect are largely analogous to those described above in connection with the first aspect. Embodiments mentioned in relation to the first aspect are largely compatible with the second aspect.

The phase or frequency comparator and the reference signal generator may form part of a phase-locked loop of the device which tracks the phase of the reflected signal.

The device may include a loop filter adapted to filter the output signal received from the phase or frequency comparator. The filtered output signal may be provided as a feedback signal to the reference signal generator wherein the reference signal generator may be adapted to vary at least one of a phase and a frequency of the adjustable reference signal based on the filtered output signal.

According to an embodiment, the signal processing circuitry is implemented in a digital signal processor. Implementing the signal processing circuitry in digital domain provides a flexibility of the device, as a digital implementation may be easily amended. Also, implementing the signal processing circuitry in digital domain may provide tracking of the phase or frequency while avoiding non-linearities that may otherwise be present in analog components.

According to an embodiment, the device may further comprise a vital sign estimator, which is arranged to receive an output from the digital signal processor and determine at least one of a heart rate or a respiratory rate based on the output from the digital signal processor.

The device may include a processing unit, which may be configured to operate as a vital sign estimator. The processing unit may be adapted to determine at least one of the heart rate and the respiratory rate by performing a frequency analysis of the output signal of the phase or frequency comparator (which may be filtered by the loop filter prior to being received at the processing unit).

BRIEF DESCRIPTION OF THE DRAWINGS

The above, as well as additional objects, features and advantages of the disclosed technology, will be better understood through the following illustrative and non-limiting embodiments of the disclosed technology, with reference to the appended drawings. In the drawings like reference numerals will be used for like elements unless stated otherwise.

DETAILED DESCRIPTION OF CERTAIN ILLUSTRATIVE EMBODIMENTS

Figure 1:
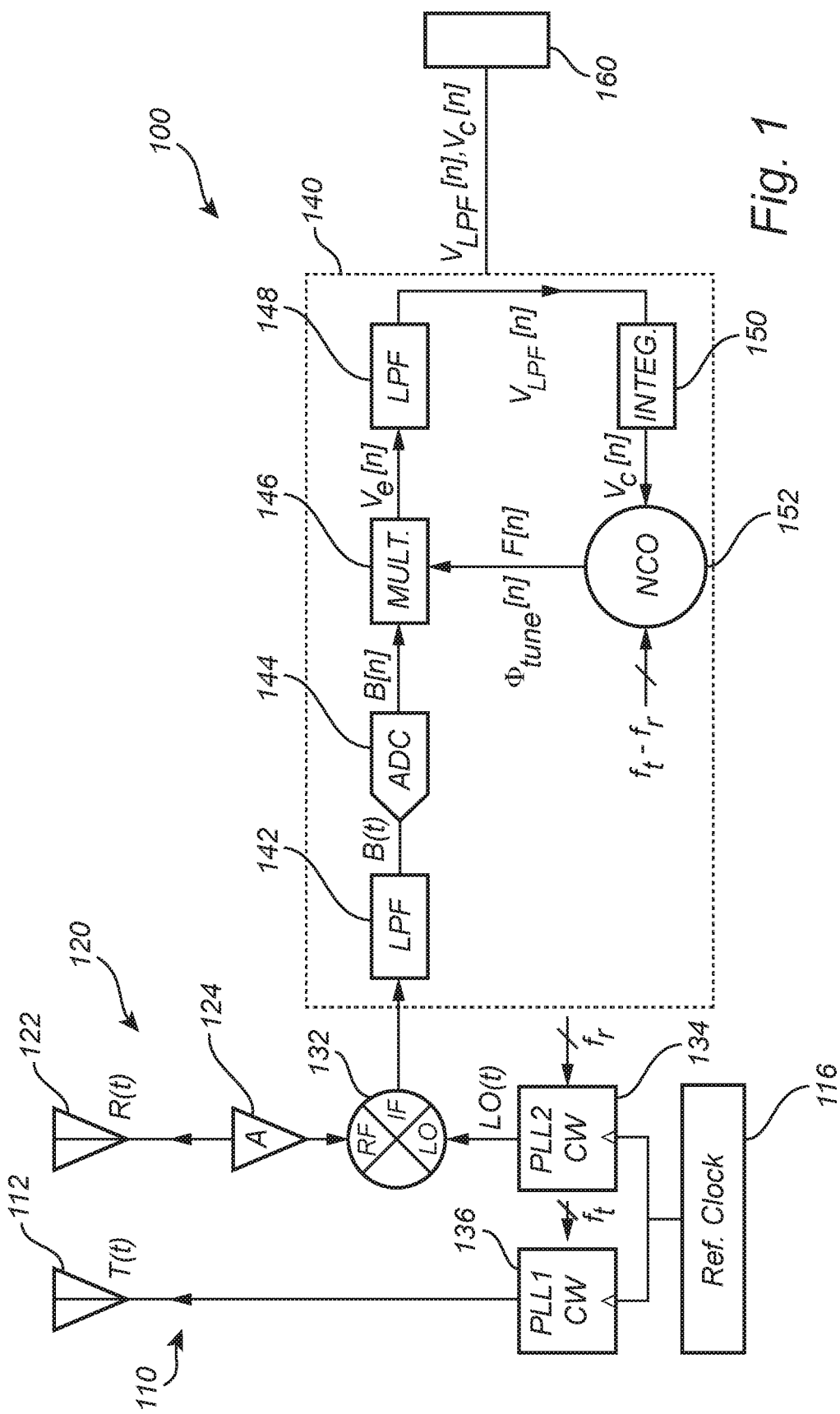
FIG. 1 is a schematic block diagram of a first device which may be used for determining a heart rate and/or a respiratory rate of a subject.

FIG. 1 is a schematic block diagram of a first device 100 which may be used for detecting and determining a heart rate and/or a respiratory rate of a subject. The subject may be a human, however the disclosed technology is equally applicable to other mammal or animal subjects. The subject may in the following also be referred to as the "target."

The device 100 includes a transmitter 110 arranged to transmit a radio frequency signal T(t) towards the subject. The signal T(t) is generated by a signal generator 136 which will be described in detail below. The signal T(t) is transmitted towards the subject via a transmitter antenna 112. The transmitter 110 may optionally include an amplifier for amplifying the signal generated by the signal generator 136 prior to transmission by the transmitter antenna 112. The transmitter 110 may, for example, be arranged to generate the signal T(t) with a frequency in the range of 300 MHz to 300 GHz.

The device 100 further includes a receiver 120 arranged to receive a radio frequency signal R(t) resulting from a reflection of the transmitted signal T(t) by the subject. The reflected signal R(t) may be received via a receiver antenna 122. The receiver 120 may optionally include an amplifier 124 for amplifying the received signal R(t) prior to demodulation thereof.

Each one of the transmitter antenna 112 and the receiver antenna 122 may for instance be arranged as a patch antenna, a beamforming antenna or a horn antenna.

For the purpose of detecting the heart rate and/or respiratory rate the transmitter 110 is advantageously oriented such that the transmitted signal T(t) is directed towards a chest region of the subject. Correspondingly, the receiver 120 is advantageously oriented such as to receive the reflected signal R(t) from the chest region of the subject.

The heartbeat and the respiration of the subject cause a respective periodic motion or displacement of the tissue in the chest region of the subject. Assuming that the subject is facing in the direction of the transmitter 110 and the receiver 120, the tissue in the chest region of the subject will, due to the heartbeat and respiration, exhibit a time-varying displacement along the direction of propagation of the transmitted signal T(t) and the reflected signal R(t). Upon reflection of the transmitted signal T(t) the displacement will result in a time-varying Doppler-shift when the reflected signal R(t) is formed. In other words, the heartbeat and the respiration of the subject will result in a modulation (which may be expressed as a time-varying frequency or phase shift) of the reflected signal R(t).

The device 100 further comprises a first reference signal generator 134, which will be described in detail below. The first reference signal generator 134 may provide a first reference signal, which may hereinafter also be called a local oscillator (LO) signal.

The reflected signal R(t) and the local oscillator signal LO(t) may be provided to a mixer 132, which may down-convert the reflected signal R(t) to an intermediate frequency $f_{IF}$, which is the difference between a transmitted frequency $f_t$ and a reference frequency $f_r$ of the local oscillator signal. The mixing of the reflected signal R(t) and the local oscillator signal LO(t) may thus provide an output signal to a signal processing circuitry 140 for analyzing the reflected signal.

The mixer may be, for instance, a diode mixer, a diode ring mixer, a switching mixer, a Gilbert cell mixer or some other type of frequency-conversion mixer. The mixer may be a balanced or double-balanced mixer.

In order to demodulate or extract the phase and/or frequency modulation of the reflected signal R(t), caused by the displacement of the tissue, the device 100 employs a signal processing circuitry 140 which implements a phase-locked loop (PLL). The PLL may operate in a phase-demodulator or frequency-demodulator configuration.

The first device 100 implements the PLL in digital domain and the signal processing circuitry 140 may thus be provided as a digital signal processor (DSP). The DSP 140 may comprise a lowpass filter 142 for passing only the down-converted baseband signal B(t) from the mixer 132. The DSP 140 may further comprise an analog-to-digital converter (ADC) 144 for converting the analog signal to digital domain forming a vital sign carrying signal B[n]. Alternatively, the lowpass filter 142 and the ADC 144 may be external to the DSP 140 and the DSP 140 may receive the vital sign carrying signal B[n] at an input of the DSP 140.

The PLL includes a phase or frequency comparator 146. The phase or frequency comparator 146 includes a first input and a second input. The phase or frequency comparator 146 may receive the vital sign carrying signal B[n] on the first input and an adjustable second reference signal F[n] on the second input. The phase or frequency comparator 146 is arranged to provide an output signal $V_e[n]$ which is indicative of a phase difference between the vital sign carrying signal B[n] and the adjustable reference signal F[n].

The PLL further includes a loop filter 148, which may receive the output signal from the phase or frequency comparator 146 and may be arranged to extract only the difference of the signals on the first and second inputs to the phase or frequency comparator 146 (and hence remove any other combinations of these signals).

The PLL may further include an integrator 150, which may receive the lowpass filtered signal. If an integrator 150 is used, the phase of the vital sign carrying signal will be tracked and the PLL will be operated in a phase-demodulator configuration. A phase-demodulator configuration allows determining a displacement of the target, as phase and displacement are related by a constant which depends on the transmitted frequency and sensitivity of a generator of the adjustable second reference signal. Thus, the use of an integrator 150 in the PLL may allow estimating a magnitude of tissue motion based on heart or respiratory action of the target based on the determined phase.

The PLL further includes a numerically controlled oscillator (NCO) 152. The NCO 152 implements a reference signal generator and provides an adjustable second reference signal F[n] as output, which is provided on the second input of the phase or frequency comparator 146. The NCO 152 thus receives a control voltage $V_c[n]$ and produces a feedback signal F[n] accordingly.

However, the integrator 150 of the PLL may also be omitted, whereby the lowpass filtered signal may be directly passed to the NCO 152. This implies that the frequency of the vital sign carrying signal will be tracked instead and the PLL will be operated in a frequency-demodulator configuration.

As will be understood by the person skilled in the art, the DSP 140 may be implemented in a number of different manners. The DSP 140 may be implemented in hardware, or as any combination of software and hardware. The DSP 140 may for instance be implemented as software being executed on a general-purpose computer, as firmware arranged, for example, in an embedded system, or as a specifically designed processing unit, such as an Application-Specific Integrated Circuit (ASIC) or a Field-Programmable Gate Array (FPGA), In a particular embodiment, the DSP 140 may be implemented as software providing algorithms for performing operations of the phase or frequency comparator 146, the loop filter 148, the integrator 150 and the NCO 152.

The implementation of the DSP 140 in software provides a high flexibility of the device 100, as the software may be easily changed. For instance, a gain of the phase or frequency comparator 146 may be changed to alter characteristics of the device 100 and adapt the device 100 to a changed set-up of detecting a vital sign.

For the purpose of detection of heart rate or respiration rate an upper limit of the frequency range of main interest may be 10-20 Hz. Accordingly, the loop filter 148 may be adapted to suppress frequencies above 10-20 Hz (i.e., by providing a cut off frequency falling in the range 10-20 Hz). However, for the purpose of obtaining a loop characteristic of the PLL such that the PLL may reliably track the frequency/phase shift of R(t) due to tissue displacement caused by the heartbeats and/or respiration, the loop filter 148 may be adapted to suppress frequencies above a threshold frequency in the range of one or a few kHz to one or two MHz (i.e., by providing a cut off frequency falling in the range 1 kHz to 2 MHz).

It should be noted that the phase or frequency comparator 146 may produce new signals at the sum and difference of the phases (frequencies) present at the first and second inputs. Since the two inputs are at the same frequency when the loop is locked, there is one output at twice the input frequency and one output proportional to a cosine of the phase difference. The loop filter 148 may also be arranged to remove the doubled frequency component.

However, if the vital sign carrying signal is provided at an intermediate frequency $f_{IF}=0$ ($f_t=f_r$), it may not be possible to separate the sum and differences of the phases and therefore distortions to the vital sign detection may be generated. Thus, the transmitted frequency $f_t$ and a reference frequency $f_r$ should differ in order to enable detection of the vital signs. The transmitted frequency $f_t$ and a reference frequency $f_r$ may be chosen such that the output signals (sum and difference of the reflected signal and the first reference signal) from the mixer 132 may be easily separated. Also, the transmitted frequency $f_t$ and a reference frequency $f_r$ may be chosen such that the difference is sufficiently high to avoid mixer flicker noise.

As shown in FIG. 1, the device 100 may comprise an oscillator 116, which may provide a reference clock signal. The reference clock signal may be provided as input to the signal generator 136 and may drive the forming of the radio frequency signal T(t) by the transmitter 110. The signal generator 136 may be implemented as a phase-locked loop, which receives the reference clock signal and input of a transmit frequency $f_t$ and generates a continuous wave radio frequency signal having the transmit frequency $f_t$.

The reference clock signal from the oscillator 116 may also be provided as input to the first reference signal generator 134. Similar to the signal generator 136, the first reference signal generator 134 may be implemented as a phase-locked loop, which receives the reference clock signal and input of a reference frequency $f_r$ and generates a continuous wave radio frequency signal LO(t) having the reference frequency $f_r$.

The reflected signal R(t) is based on the transmitted signal T(t). Since the transmitted signal T(t) and the first reference signal LO(t) are formed on basis of input from the same oscillator 116, the reflected signal R(t) and the first reference signal LO(t) are partially correlated and residual phase noise may therefore insignificantly influence the vital sign carrying signal B[n].

In use of the device 100 for detecting heart rate and/or respiratory rate of a subject, a radio frequency signal T(t) is transmitted by the transmitter 110 towards the chest region of the subject. The transmitted signal T(t) is reflected by tissue of the chest region of the subject. The reflected signal R(t) is received by the receiver 120. As described above, the reflected signal R(t) will be modulated by the time-varying displacement of the tissue emitting the reflected signal R(t).

The total tissue displacement x(t) due to heartbeat and respiration of the subject may be expressed as:

$$x(t)=x_l(t)+x_h(t)=X_l \sin(2\pi f_l t)+X_h \sin(2\pi f_h t) \quad \text{(Equation 1)}$$

where $x_l(t)$ and $x_h(t)$ indicate respectively the mechanical displacements produced by the respiration and the heart. As shown in Equation 1, $x_l(t)$ and $x_h(t)$ may be approximated as periodic functions, where $X_l$ and $X_h$ are the maximum mechanical displacements caused by the expansion and contraction of the lungs and the heart and $f_l$ and $f_h$ are the vital signs frequencies which represent information that may be desired to be determined. $X_l$ and $X_h$ may for instance on average be about 0.5-10 mm and 0.05-0.1 mm, respectively, for an adult. Depending on the subject and on the health condition, $f_l$ and $f_h$ generally are within 0.1-3 Hz. These ranges however only represent non-limiting examples and the system 100 is usable for detection of heart rate and/or respiratory rate in even broader ranges of tissue displacement amplitudes and frequencies. It should also be noted that the above approximation is only provided as an example to facilitate understanding of the principles of the disclosed technology and the disclosed technology is not dependent on a particular choice of approximation.

The reflected signal R(t) is (subsequent to the mixing with the first reference signal) provided to the first input of the phase or frequency comparator 146 where B[n] is compared to the feedback signal F[n] provided to the second input of the phase or frequency comparator 146. As described above, the feedback signal F[n] tracks the phase of the downconverted reflected signal R(t). Therefore, the output signal $V_e[n]$ of the phase or frequency comparator 146 becomes proportional to the modulations induced by the time-varying displacement of the tissue.

The vital sign carrying signal B[n] can be expressed as:

$$B[n] = C(t_n) \cos\left[2\pi f_{IF} t_n + \frac{4\pi x(t_n)}{\lambda} + \frac{4\pi d_0}{\lambda} + \theta + \Delta\phi(t_n)\right] \quad \text{(Equation 2)}$$

where n is the $n^{th}$ sample acquired at a sampling instant $t_n=n/f_s$, where $f_s$ is a sampling frequency, $C(t_n)$ is the voltage amplitude modulated by the target motion, $d_0$ is a mean distance between the antennas 112, 122 and the target, $\lambda$ is the wavelength of $f_t$, $\theta$ takes into account phase shift at the target surface and the phase offsets between radio blocks and is normally fixed, while $\Delta\phi(t_n)$ is residual phase noise which may be insignificant and neglected, for example since LO(t) and R(t) are partially correlated, as explained above.

When the lock condition of the PLL is satisfied, the feedback signal can be expressed as:

$$F[n]=\sin(2\pi f_{IF} t_n+\phi_{tune}[n]) \quad \text{(Equation 3)}$$

where $\phi_{tune}[n]=K_{NCO}*V_e[n]$ is the phase change necessary to track the phase modulation produced by the target and $K_{NCO}$ is sensitivity of the NCO 152 (rad/V). When the lock condition of the PLL is achieved, the phase of the feedback signal F[n] equals the phase of the vital sign carrying signal B[n], which may be expressed as:

$$LB[n] = \qquad \qquad \text{(Equation 4)}$$

$$2\pi f_{IF} t_n + \frac{4\pi x(t_n)}{\lambda} + \frac{4\pi d_0}{\lambda} + \theta = LF[n] = 2\pi f_{IF} t_n + \phi_{tune}[n].$$

Thus, $\phi_{tune}[n]$ is a copy of the phase of the vital sign carrying signal B[n] and the time-varying displacement of tissue may be extracted accurately from the output signal $V_e[n]$ of the phase or frequency comparator 146. The output signal $V_e[n]$ may be filtered by the loop filter 148 to form a filtered signal $V_{LPF}[n]$ wherein the doubled frequency component is removed so as to further facilitate extraction of the time-varying displacement of tissue.

A derivative of the phase may be expressed as:

$$\frac{\phi_{tune}[n] - \phi_{tune}[n-1]}{\frac{2\pi}{fs}} = \frac{2}{\pi} \frac{x(t_n) - x(t_{n-1})}{\frac{1}{fs}} = f_{tune}[n]. \qquad \text{(Equation 5)}$$

The expression in Equation 5 shows that $f_{tune}[n]$ is proportional to a frequency of B[n] by which speed information of the target may be estimated.

The characterization of the phase change signal $\phi_{tune}[n]$ in Equation 4 is valid on a condition that the position of the subject is fixed in relation to the device 100. However, a main advantage of the device 100 is that it may be used for detecting the heart rate and/or respiration rate even in a non-idealized scenario wherein the distance between the subject/target (also chest wall) and the system 100 is not fixed. This may be understood by considering the effect of a step change of the distance between the subject and the device 100. A step change of the distance will result in a step change of the phase difference between the vital sign carrying signal B[n] and the second reference signal F[n]. The PLL of the DSP 140 will respond to the step change of the phase difference by changing the phase of the first reference signal F[n] to track the phase difference. After a transient (the duration of which is determined by the dynamics of the PLL) the PLL of the DSP 140 will reacquire a lock wherein the reference signal F[n] will catch up/fall back with the phase of the reflected signal R(t).

The static target distance $d_0$ will produce a DC level on top of which there is a modulation based on vital signs. This implies that in a steady state, the phase modulation based on vital signs may be extracted as being centered around the fixed phase shift. If the target changes position, the PLL can track this change and the vital signs will be centered to a new DC level due to the new target position.

As may be understood, this discussion is equally applicable to other sources for static and semi-static phase offsets, such as radio block delay. The PLL of the DSP 140 will hence force the receiver 120 to operate at its optimum point, which corresponds to the point where a phase difference between the vital sign carrying signal B[n] and the feedback signal F[n] is relatively small, wherein the signal level of the low-frequency components of the output signal $V_e[n]$ will be close to zero.

In the event that the chest region of the subject undergoes a periodic movement along the direction of propagation of the transmitted signal T(t) and the reflected signal R(t), it follows from the above that the signal $\phi_{tune}[n]$ may be expressed as:

$$\phi_{tune}[n] = \frac{4\pi x_h(t_n)}{\lambda} + \frac{4\pi x_l(t_n)}{\lambda} + \frac{4\pi d(t_n)}{\lambda} + \theta \qquad \text{(Equation 6)}$$

where the additional term $d(t_n)$ represents a variation of the target distance about the mean distance $d_0$, wherein the variation is not due to the vital signs. This variation may be periodic or may be any arbitrary movement, which need not be centered to a specific position. Arbitrary movements may be handled as a transient as discussed above in relation to shifting of the target distance $d_0$. A period variation may also be handled and may be expressed as:

$$d(t) = X_s \sin(2\pi f_s t) \qquad \text{(Equation 7)}$$

where $X_s$ represents the maximum amplitude of the periodic variation of the subject distance and $f_s$ represents the frequency of the variation. Since the signal $\phi_{tune}[n]$ is free from any cross terms between the heart rate, the respiration rate and the periodically varying target distance, the respective frequencies of the vital signs may be readily distinguished and extracted even in the presence of periodic subject movements. Provided a frequency of the periodic subject movements falls outside the typical range of frequencies of the heart rate and the respiration rate, the signal contribution due to periodic subject movements may even be removed from $\phi_{tune}[n]$ by filtering based on a priori knowledge of standard ranges of the heart rate and the respiration rate. The filtering may be arranged to pass frequencies in each of the standard ranges of the heart rate and the respiration rate to also enable removing a frequency of a periodic variation therebetween.

The output signal $V_e[n]$ of the phase or frequency comparator 146 represents the frequency variations (i.e., the frequency modulation) of the vital sign carrying signal B[n] resulting from the tissue displacement due to the heart beat and respiration (and other periodic chest region movement), if any. The corresponding phase variations (i.e., the phase modulation) may be directly extracted from the phase change signal $\phi_{tune}[n]$ generated by the NCO 152. The phase variations are also represented by the integrated signal $V_c[n]$, which is proportional to the phase variations through $K_{NCO}$, and hence phase variations may also be extracted from the integrated signal. This may be used in analog implementations of the PLL, as discussed below, where the phase change signal $\phi_{tune}[n]$ is not directly available to be extracted.

The phase information allows demodulating phase of the vital sign carrying signal so that instantaneous displacement of the target may be determined. The phase information may be available in the phase change signal $\phi_{tune}[n]$ of the DSP 140, even if the PLL is set to be frequency-demodulating. However, in analog implementations of the PLL, as discussed below, if no integrator 150 is included in the PLL, the vital sign carrying signal may be frequency demodulated allowing estimating only a frequency of the heart or respiratory action.

The device 100 allows extracting linearly the phase modulation produced by the target. Thus, a magnitude of tissue motion based on heart or respiratory action and/or a heart rate or respiratory rate may be determined based on the signal processing performed by the device 100. The device 100 enables the extraction of the phase modulation while avoiding the null point and small angle approximation issues.

This may also be confirmed by considering the situation when the lock condition of the PLL is satisfied. Then the phase difference $\phi_e[n]$ (or the frequency difference) between B[n] and F[n] is such that output of the phase or frequency comparator 146 is essentially zero. This means that the feedback signal F[n] forces the phase or frequency comparator 146 to operate in a linear region, where it is possible to consider $\sin(\phi_e) \approx \phi_e$.

For the purpose of detecting the magnitude of tissue motion, the heart rate and/or the respiratory rate, the device 100 may further include a vital sign estimator 160. The vital sign estimator 160 may be arranged to receive the phase change signal $\phi_{tune}[n]$, the filtered output signal $V_{LPF}[n]$ and/or the integrated signal $V_c[n]$ as input. The vital sign estimator 160 may be implemented as a separate processing unit receiving input from the DSP 140 or may be integrated in a common processing unit that may perform the operations of the DSP 140 and the vital sign estimator 160.

The vital sign estimator 160 may be arranged to determine or estimate the heart rate and/or the respiratory rate by performing a frequency analysis of the signal $V_{LPF}[n]$ or $V_c[n]$. The frequency analysis may include determining a frequency of at least one frequency component of the signal $V_{LPF}[n]$ or $V_c[n]$ within a given frequency interval. The frequency component(s) may be respective frequency components of the signal $V_{LPF}[n]$ or $V_c[n]$ which fall within the given frequency interval and which have a respective amplitude which exceeds a threshold level. The frequency interval may correspond to an expected frequency range of the vital sign(s) to be determined, i.e., the heart rate and/or the respiratory rate. The frequency interval may for example be 0.1-3 Hz. The threshold level may be set such that the influence of noise is minimized without reducing the sensitivity of the measurement too much. The vital sign estimator 160 may output the determined frequency/frequencies as an estimate of the heart rate and/or respiratory rate. The vital sign estimator 160 may identify the component of the two components having the lowest frequency as the respiration rate and the other component as the heart rate. The output may for example be presented on a display connected to the device 100 or stored in a storage device for further analysis and post-processing. The vital sign estimator 160 may further be arranged to estimate a magnitude of a tissue displacement due to at least one of the heart rate and the respiratory rate by determining an amplitude of a frequency component of the integrated output.

It should also be realized that the vital sign estimator 160 may be arranged to analyze the signals in other manners. For instance, the analysis may be performed in time domain by using filters to separate the frequencies $f_l$ and $f_h$ and then determine the time domain signals to estimate the vital signs.

In a more basic implementation the vital sign estimator 160 may simply be adapted to detect whether a heart rate and/or a respiratory rate is present, for example by determining if the frequency interval includes any component(s) of an amplitude exceeding a (respective) threshold level. The vital sign estimator 160 may accordingly output a signal indicating whether such components were detected or not.

Referring now to FIGS. 2-8, several different embodiments of a device for detecting a vital sign will be described. The devices of these embodiments have many features in common with the device 100 shown in FIG. 1, and in the following description, mainly differing features will be described.

Figure 2:
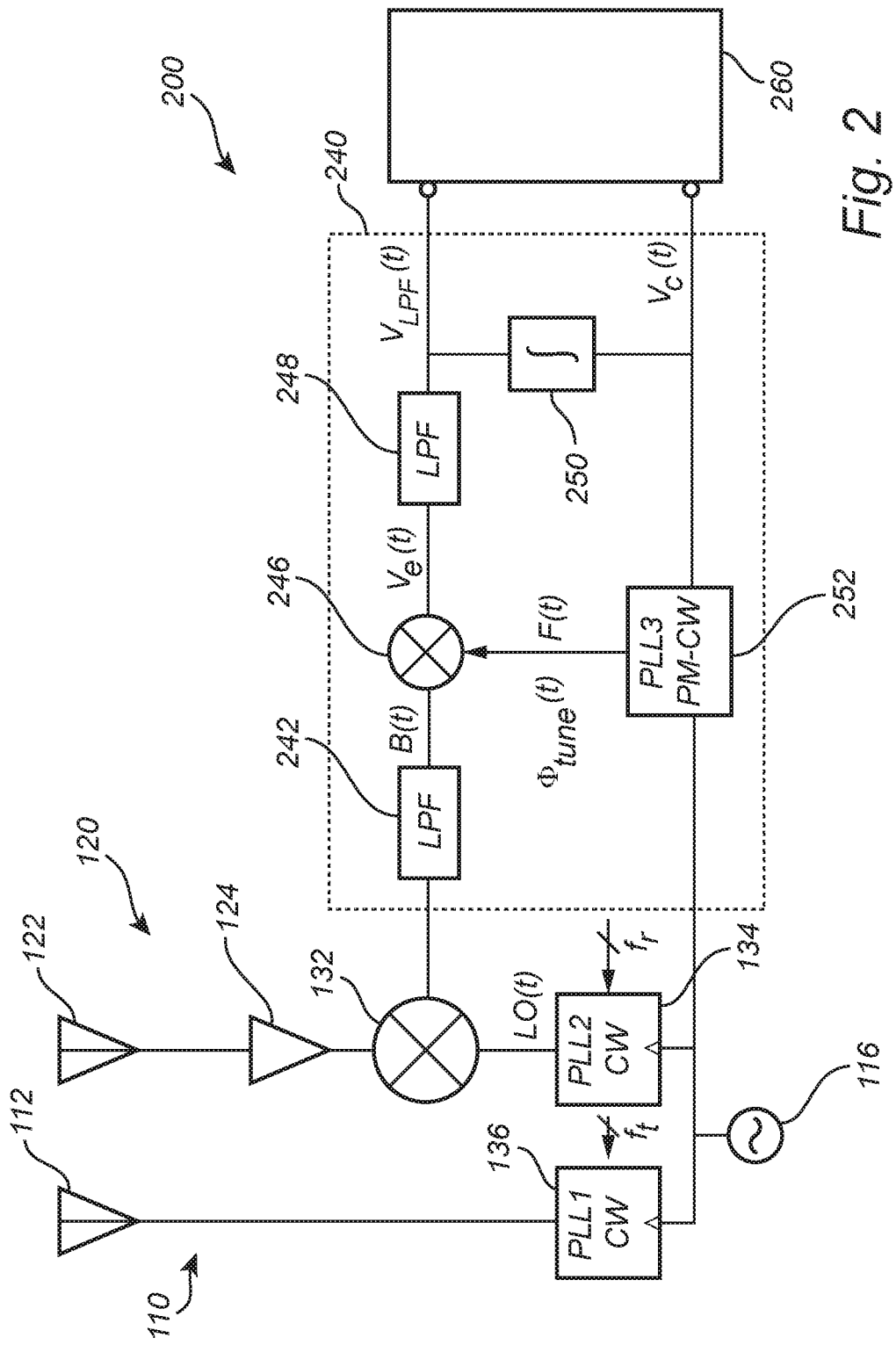
FIG. 2 is a schematic block diagram of a second device which may be used for determining a heart rate and/or a respiratory rate of a subject.

In FIG. 2, an analog device 200 is shown. Thus, the device 200 is very similar to the device 100 shown in FIG. 1. However, instead of using a DSP 140, an analog signal processing circuitry 240 is used for implementing a phase-demodulating circuitry that receives the down-converted reflected signal R(t) from the mixer 132.

The analog signal processing circuitry 240 comprises analog components for implementing a PLL. Thus, the analog signal processing circuitry 240 comprises a lowpass filter 242 passing the downconverted vital sign carrying signal B(t) to a phase or frequency comparator 246. The phase or frequency comparator 246 may be implemented as a mixer. However other types of phase or frequency comparators 246 may also be used such as a phase-frequency detector, a charge-pump phase detector or an exclusive-OR type of phase comparator.

The signal processing circuitry 240 further comprises a lowpass filter 248, an integrator 250 and an adjustable reference signal generator 252. The adjustable reference signal generator 252 may be formed as a PLL, which is connected to the oscillator 116 (so that residual phase noise may still be neglected). The PLL 252 receives a control voltage $V_c(t)$ from the integrator 250 and produces a phase-modulated feedback signal F(t) accordingly, which is then provided at the second input of the phase or frequency comparator 246.

The lowpass filtered signal of the output signal $V_{LPF}(t)$ and the integrated signal $V_c(t)$ may be output respectively from the signal processing circuitry 240 in order to allow extracting vital signs from the output signals. A vital sign estimator 260 may then be implemented in a processing unit, whereby the signals may first be analog-to-digital converted, or the vital sign estimator 260 may be implemented in analog circuitry for determining vital signs.

Figure 3:
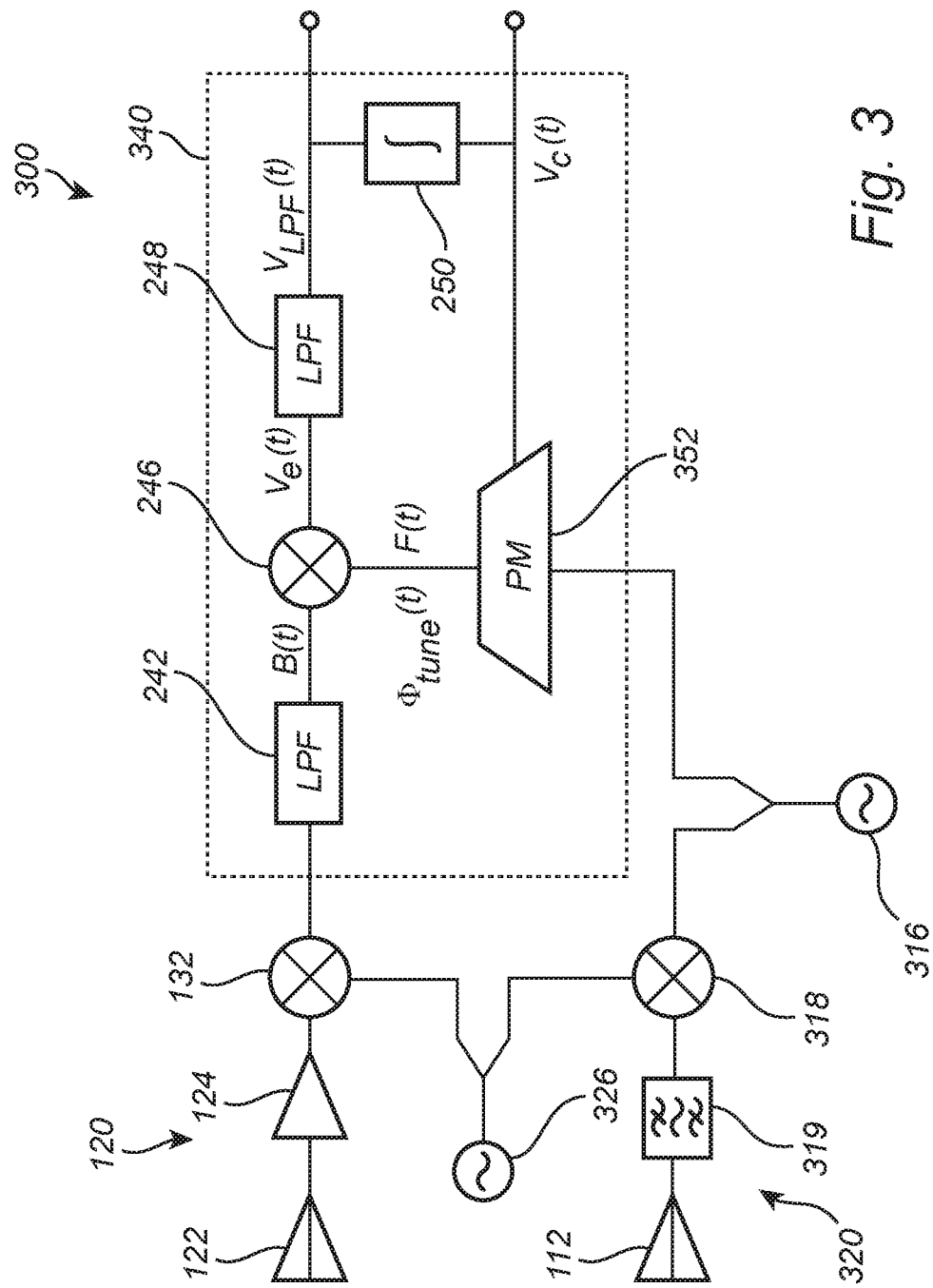
FIG. 3 is a schematic block diagram of a third device which may be used for determining a heart rate and/or a respiratory rate of a subject.

In FIG. 3, a similar analog device 300 is shown, wherein the signal processing circuitry 340 is very similar to the device 200 in FIG. 2. However, the device 300 is arranged to generate signals in a different manner compared to the devices 100, 200 discussed above.

The device 300 comprises a first local oscillator 316 and a second local oscillator 326. The transmitter 320 comprises a mixer 318, which receives a signal from the first local oscillator 316 on a first input and a signal from the second local oscillator 326 on a second input. The mixer 318 may then produce a signal which comprises combinations of the frequencies of the signals from the first and second local oscillators 316, 326. The signal from the mixer 318 may be further passed through a bandpass filter 319 for selecting a desired frequency output by the mixer 318. The bandpass filter 319 could also be a lowpass filter or a highpass filter. Thus, a single-tone continuous-wave radio frequency signal T(t) may be passed to the transmitter antenna 112.

Further, the first reference signal generator may be implemented by the second local oscillator 326. The second local oscillator 326 may thus provide the local oscillator signal LO(t) which may be provided to the mixer 132 for down-converting the reflected signal R(t). Since the second local oscillator 326 is used both in generating the local oscillator signal LO(t) and in generating the transmitted signal T(t), a simple set-up may be used.

The signal processing circuitry 340 of the device 300 corresponds to the signal processing circuitry 240 of the device 200, except that the adjustable reference signal generator 352 now receives a signal from the first local oscillator 316 as input for generating the phase-modulated feedback signal F(t). Thus, the first local oscillator 316 may be re-used and provide a signal which may be used both in generating the feedback signal F(t) and in generating the transmitted signal T(t).

It should be realized that the manner of generating the transmitted signal T(t) and the first reference signal LO(t) shown in FIG. 3 may also be employed in the device 100 shown in FIG. 1.

Figure 4:
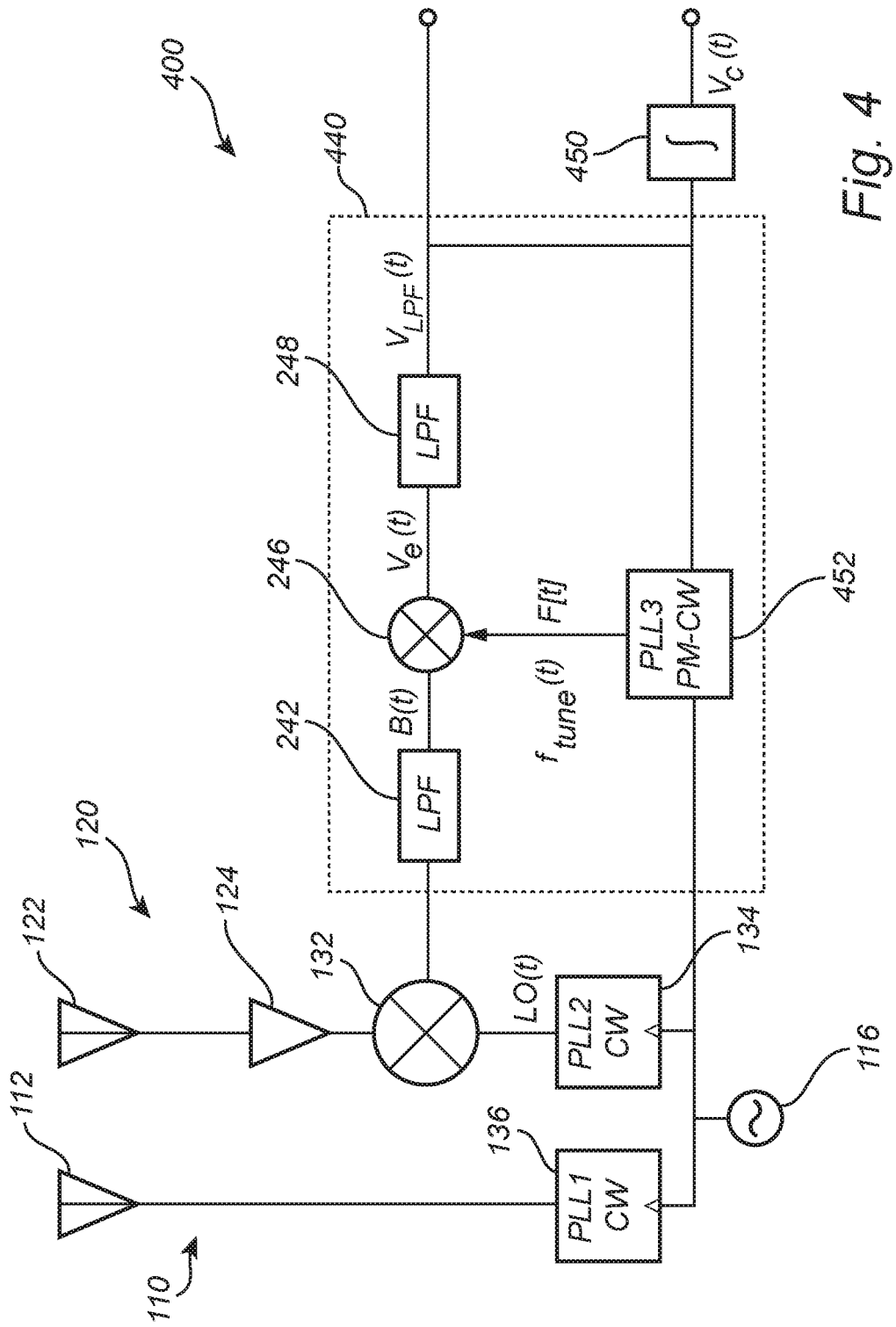
FIG. 4 is a schematic block diagram of a fourth device which may be used for determining a heart rate and/or a respiratory rate of a subject.

In FIG. 4, another analog device 400 is shown. The device 400 corresponds to the device 200 of FIG. 2, except that the signal processing circuitry 440 is arranged for tracking a frequency of the vital sign carrying signal B(t) instead of tracking the phase. Thus, there is no integrator arranged in the signal processing circuitry 440 and the adjustable reference signal generator 452 is arranged to provide a frequency-modulated feedback signal F(t). An integrator 450 may be arranged at an output of the signal processing circuitry 440 for integrating the output signal and providing corresponding phase variations to the frequency variations of the output signal $V_e(t)$.

Figure 5:
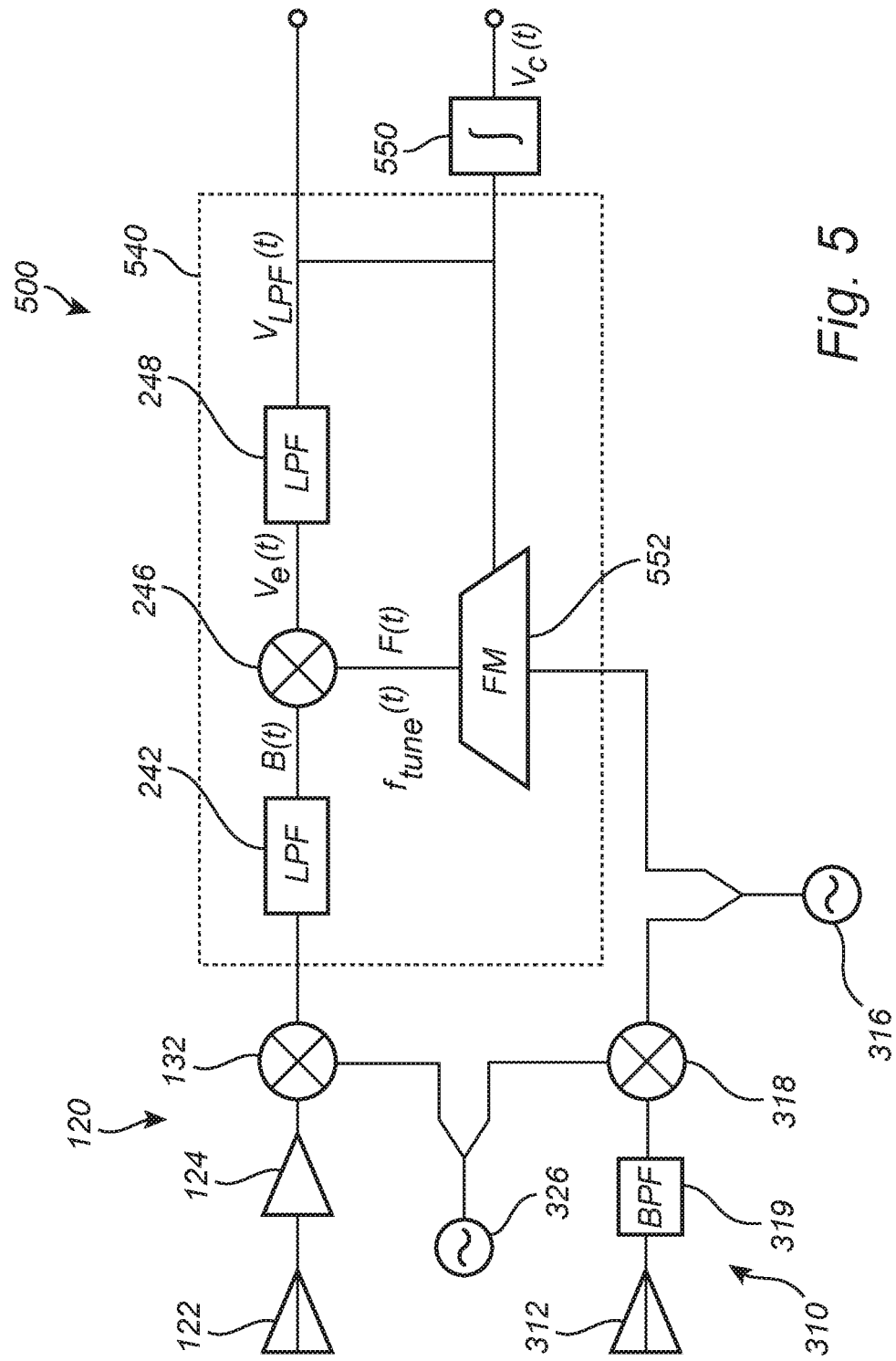
FIG. 5 is a schematic block diagram of a fifth device which may be used for determining a heart rate and/or a respiratory rate of a subject.

Similarly, in FIG. 5, yet another analog device 500 is shown. The device 500 corresponds to the device 300 of FIG. 3, except that the signal processing circuitry 540 is arranged for tracking a frequency of the vital sign carrying signal B(t) instead of tracking the phase. Thus, similar to the device 400, there is no integrator in the signal processing circuitry 540 and the adjustable reference signal generator 552 is arranged to provide a frequency-modulated feedback signal F(t). An integrator 550 may be arranged at an output of the signal processing circuitry 540.

Figure 6:
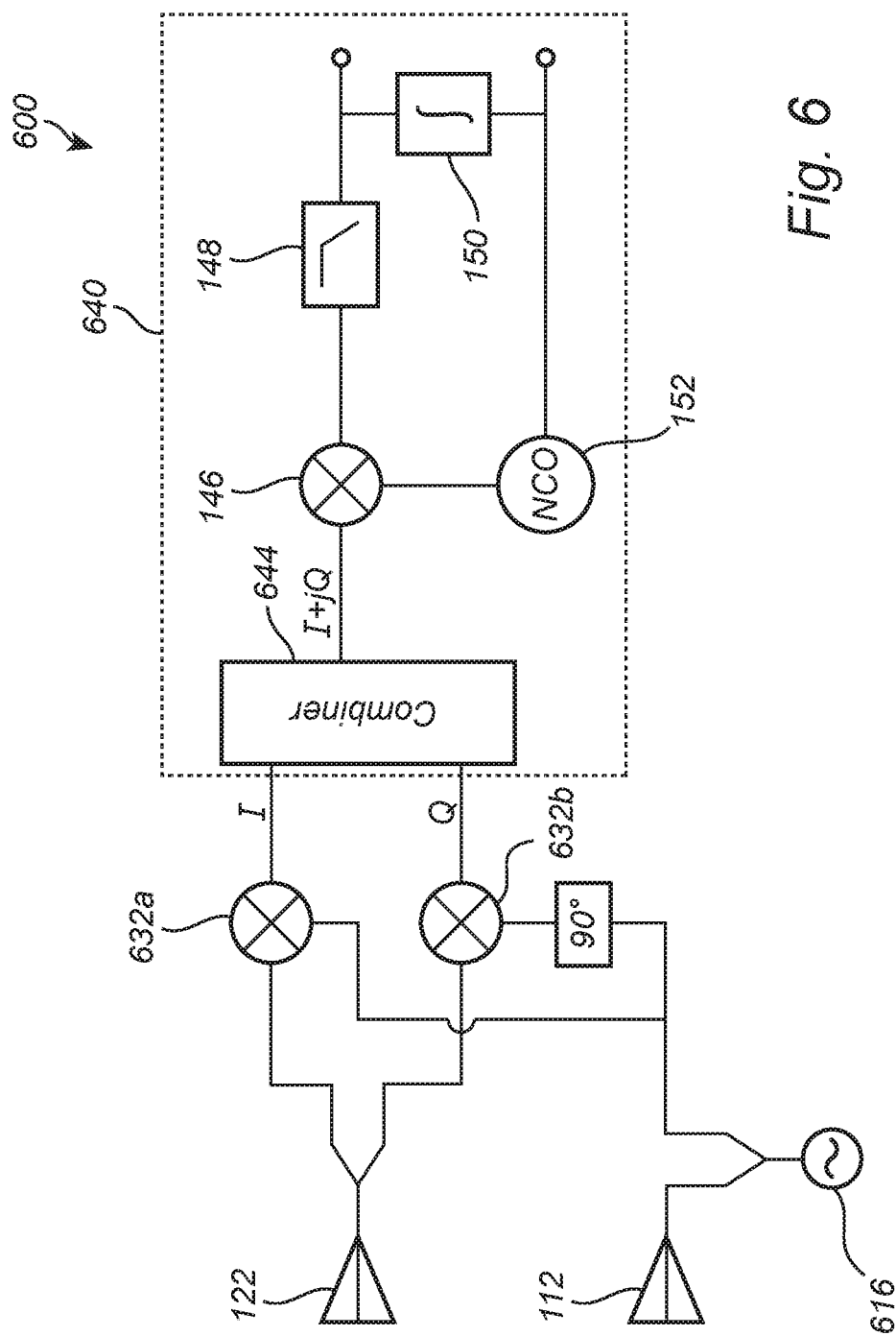
FIG. 6 is a schematic block diagram of a sixth device which may be used for determining a heart rate and/or a respiratory rate of a subject.
Figure 7:
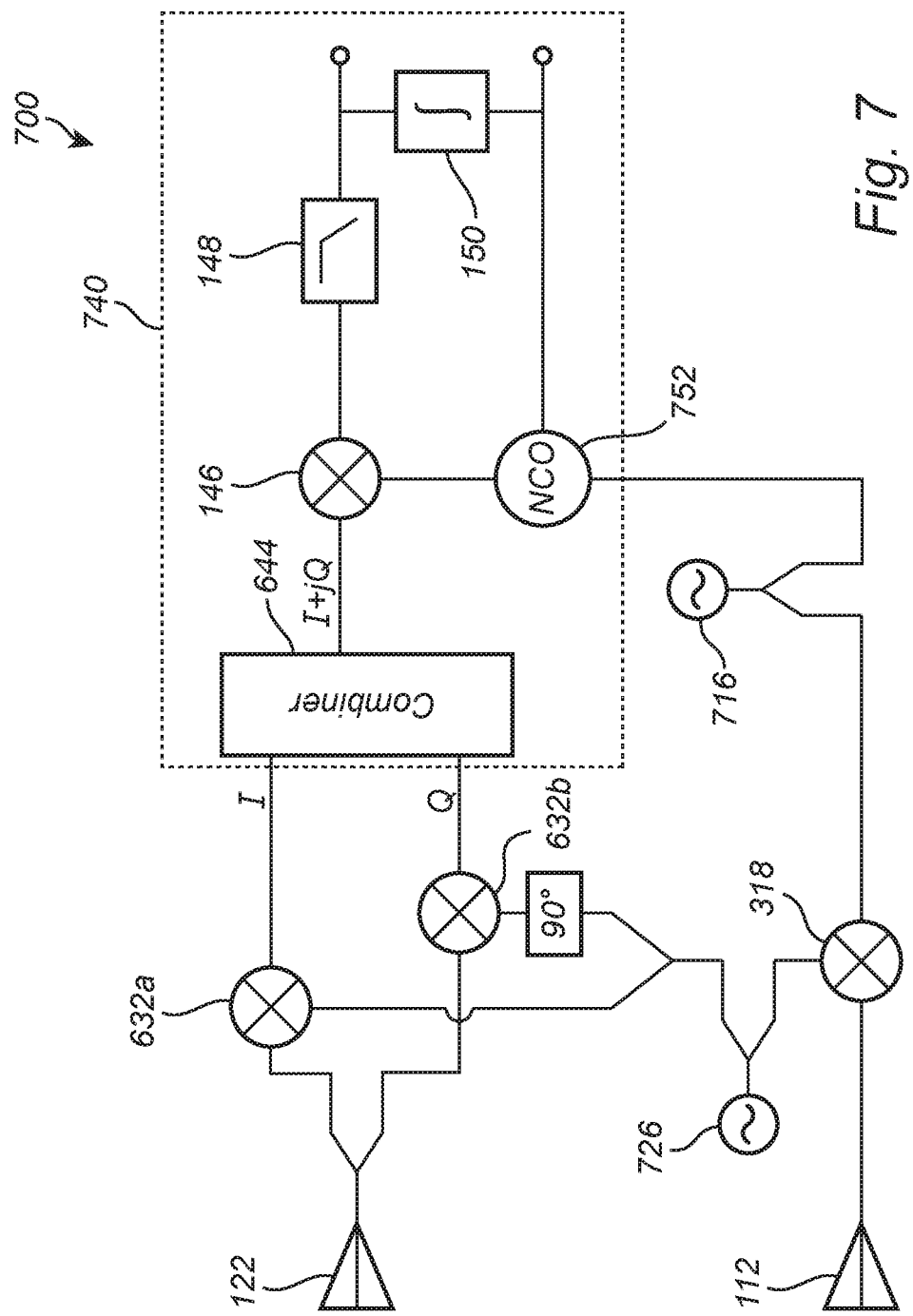
FIG. 7 is a schematic block diagram of a seventh device which may be used for determining a heart rate and/or a respiratory rate of a subject.
Figure 8:
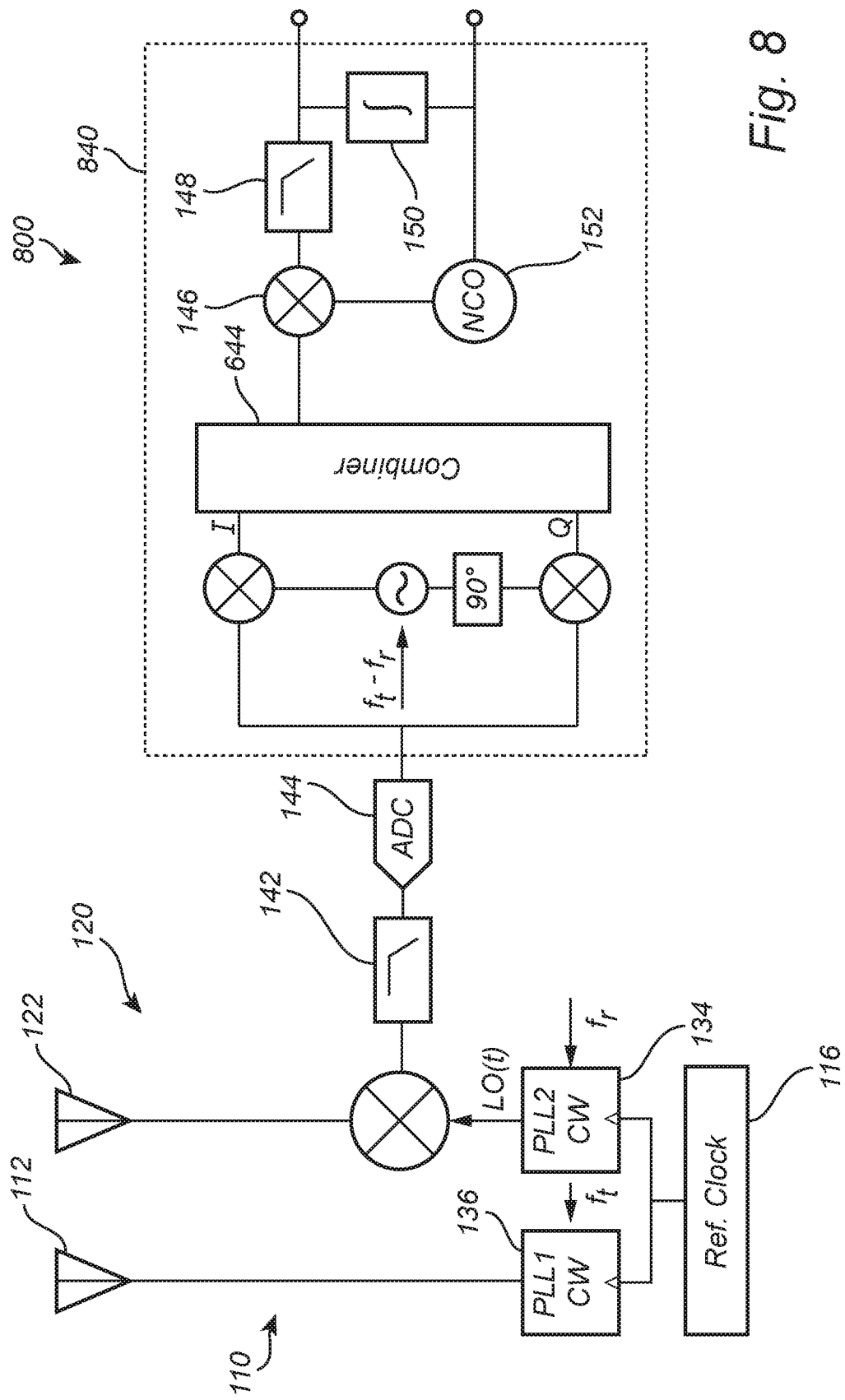
FIG. 8 is a schematic block diagram of an eighth device which may be used for determining a heart rate and/or a respiratory rate of a subject.

Referring now to FIGS. 6-8, quadrature architectures of the device are shown. The quadrature architectures provide a similar approach to demodulating information as shown in the devices of FIGS. 1-5. Thus, in comparison to prior art vital sign detection using quadrature architecture, the device does not need to use phase unwrapping algorithms or a differentiate and crossmultiply algorithm.

With the quadrature architecture, the reflected signal can be downconverted in baseband ($f_{IF}$=0 Hz), as it is possible to separate the sum and difference of the phases because the inphase and quadrature channels are combined in a complex form.

Thus, in FIG. 6, a device 600 is shown, wherein a local oscillator 616 is used for generating the transmitted signal T(t). The local oscillator 616 is also used for generating a first reference signal.

The received signal is divided into two channels for forming an inphase and a quadrature signal. Then, a first mixer 632a mixes the received signal with the first reference signal from the local oscillator 616 so as to form an inphase signal I. A second mixer 632b mixes the received signal with a first reference signal based on a 90° shifting of the signal from the local oscillator 616 so as to form a quadrature signal Q.

The device 600 may further comprise a signal processing circuitry 640, which may be implemented in digital domain. The signal processing circuitry may comprise a combiner 644, which receives the inphase signal I and quadrature signal Q after mixing and forms a complex form digital signal I+jQ. The digital signal processing circuitry 640 may further comprise a digital implementation of a PLL corresponding to the digital signal processing circuitry 140 of the device 100.

As shown in FIG. 7, a quadrature architecture device 700 may alternatively be arranged to generate the transmitted signal T(t) and the first reference signal in a similar way as used by the device 300. Thus, the device 700 may comprise a first oscillator 716 and a second oscillator 726. The first oscillator 716 may provide input to the NCO 752 of the signal processing circuitry 740 for generating the feedback signal F[n].

As shown in FIG. 8, a quadrature architecture device 800 may according to a further alternative be arranged to generate the transmitted signal T(t) and the first reference signal in a similar way as used by the device 100. In the device 800, a vital sign carrying signal formed by mixing the reflected signal with the first reference signal is divided into two channels in digital domain. Then, the vital sign carrying signal may be mixed with a signal from a local oscillator having the intermediate frequency $f_{IF}$ for forming an inphase signal I. Further, the vital sign carrying signal may be mixed with a signal from the local oscillator being shifted 90° so as to form a quadrature signal Q. The inphase signal I and the quadrature signal Q may then be combined to form a complex form digital signal I+jQ. The digital signal processing circuitry 840 may further comprise a digital implementation of a PLL corresponding to the digital signal processing circuitry 140 of the device 100.

Figure 9:
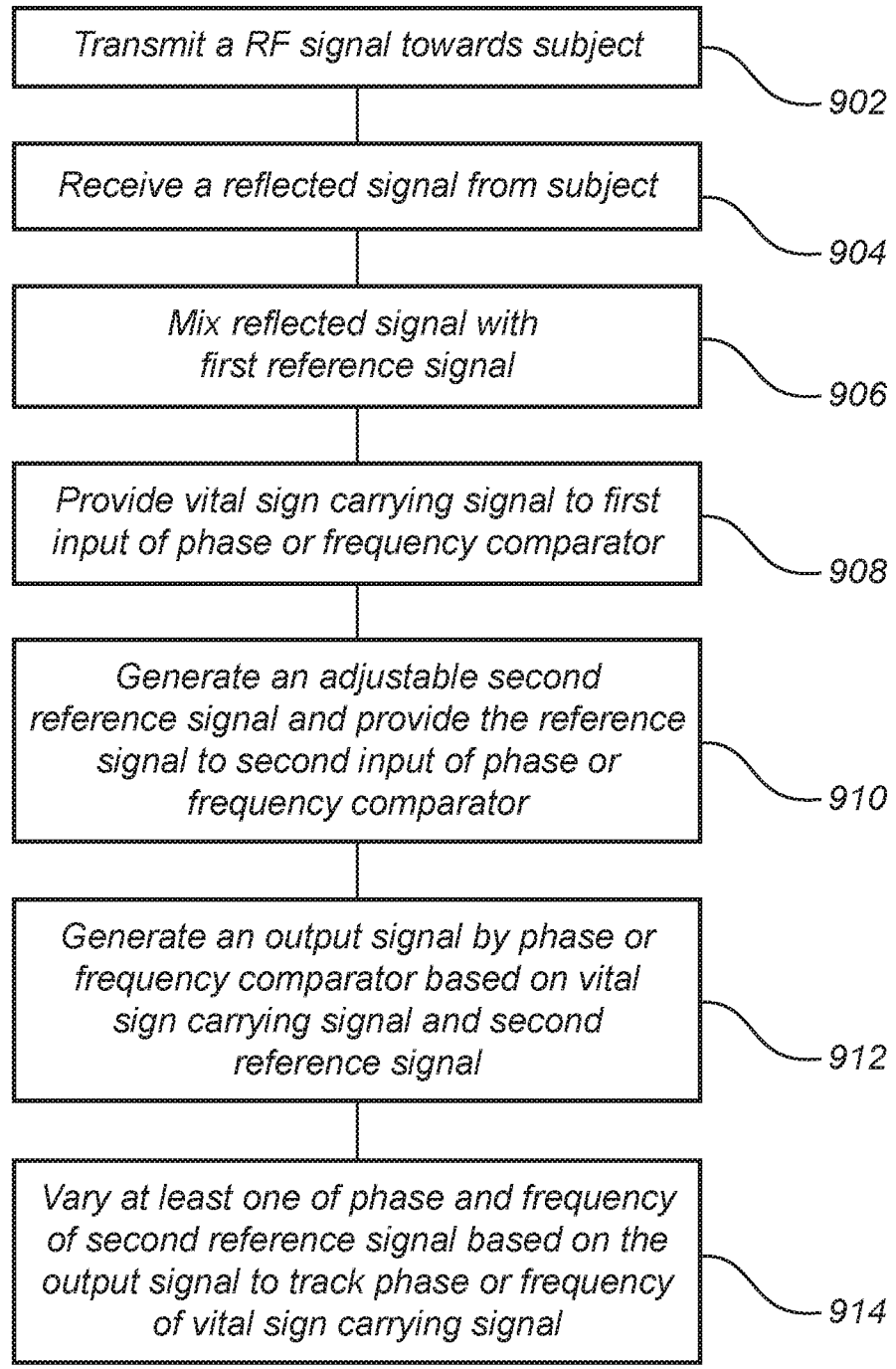
FIG. 9 is a flowchart of a method according to an embodiment.

Referring now to FIG. 9, a method for detecting a vital sign will be summarized.

The method comprises transmitting 902 a radio frequency signal towards the subject. The method further comprises receiving 904 a reflected signal from the subject, wherein the transmitted signal is reflected by the subject and Doppler-shifted due to at least one of the heart rate and the respiratory rate of the subject to form the reflected signal.

The method further comprises mixing 906 the reflected signal with a first reference signal. The mixed signal may be further processed, for example lowpass filtered and/or analog-to-digital converted, to generate a vital sign carrying signal. The vital sign carrying signal is provided 908 to a first input of a phase or frequency comparator.

The method further comprises generating 910 an adjustable second reference signal by a reference signal generator and providing the reference signal to a second input of the phase or frequency comparator. Thus, the phase or frequency comparator may generate 912 an output signal based on the vital sign carrying signal and the second reference signal. The output signal may be further processed, for example, by lowpass filtering and/or integration, before being provided back to the reference signal generator in a loop.

The reference signal generator may further vary 914 at least one of a phase and a frequency of the adjustable second reference signal based on the output signal of the phase or frequency comparator to track a phase or frequency of the vital sign carrying signal.

Thus, a phase and/or frequency of the vital sign carrying signal may be extracted and the output signal of the phase or frequency comparator may be output to a vital sign estimator for determining a vital sign of the subject.

In the above the disclosed technology has mainly been described with reference to a limited number of examples. However, as is readily appreciated by a person skilled in the art, other examples than the ones disclosed above are equally possible within the scope of the disclosed technology.

For example, the various electronic elements of the devices 100-800 may be implemented in one or more integrated circuits. Furthermore, the devices 100-800 employ a separate transmitter antenna 112 and a separate receiver antenna 122. However, it is equally possible to instead arrange the transmitter 110 and the receiver 120 to transmit/receive via a common antenna. The transmitter 110 and the receiver 120 may be connected to a common antenna via a circulator or coupler arranged to direct transmitted signals T(t) from the transmitter 110 (for example from the transmission output of the signal generator 136 or from the output of the amplifier if present) to the common antenna and to direct reflected signals R(t) from the common antenna to the receiver 120 (for example to an input of the mixer 132 or to an input of the amplifier 124 if present). Hence the same antenna may be used for both transmission of the signal T(t) and for reception of the reflected signal R(t).

What is claimed is:

1. A device for detecting a vital sign comprising at least one of a heart rate and a respiratory rate of a subject, comprising:
    a transmitter arranged to wirelessly transmit a radio frequency signal towards the subject, wherein the radio frequency signal transmitted towards the subject is a fixed-frequency signal;
    a receiver arranged to receive a reflected signal from the subject, wherein the transmitted signal is reflected by the subject and Doppler-shifted due to at least one of the heart rate and the respiratory rate to form the reflected signal;
    a mixer for mixing the reflected signal with a first reference signal so as to provide an intermediate frequency signal; and
    a signal processing circuitry comprising a phase or frequency comparator and a reference signal generator and that is configured to implement a phase-locked loop (PLL) and to receive the intermediate frequency signal,
    wherein the phase or frequency comparator is configured to receive a vital sign carrying signal based on the mixing of the reflected signal with the first reference signal on a first input and receive an adjustable second reference signal from the reference signal generator on a second input of the phase or frequency comparator, the phase or frequency comparator further configured to generate an output signal based on the vital sign carrying signal and the second reference signal, and wherein the reference signal generator is configured to vary at least one of a phase and a frequency of the adjustable second reference signal based on the output signal of the phase or frequency comparator to track a phase or frequency of the vital sign carrying signal and wherein the transmitter and receiver are configured to operate as a Doppler radar.

2. The device according to claim 1, wherein the signal processing circuitry is implemented in a digital signal processor.

3. The device according to claim 2, further comprising a vital sign estimator configured to receive an output from the digital signal processor and determine at least one of a heart rate or a respiratory rate based on the output from the digital signal processor.

4. The device according to claim 1, wherein the PLL further comprises an integrator and functions as a phase demodulator.

5. The device according to claim 3, wherein the vital sign estimator is further configured to estimate a magnitude of a tissue displacement due to at least one of heart rate and respiratory rate by determining an amplitude of a frequency component of the output from the digital signal processor.

6. The device according to claim 3, wherein the vital sign estimator is configured to perform a frequency analysis.

7. The device according to claim 1, wherein the PLL is configured to function as a demodulator.

8. The device according to claim 1, wherein a frequency of the first reference signal is different from a frequency of the transmitted signal.

9. The device according to claim 1, wherein the intermediate frequency signal output by mixing of the reflected signal with the first reference signal is converted into the digital domain.

10. The device according to claim 9, wherein the phase or frequency comparator and the reference signal generator operate in the digital domain, and wherein the reference signal generator comprises a numerically controlled oscillator.

11. The device according to claim 1, wherein the received reflected signal is divided into an inphase and a quadrature component.

12. The device according to claim 11, wherein the vital sign carrying signal is a complex form combination of the inphase and the quadrature components.

13. The device according to claim 1, wherein the transmitted signal is generated by a first phase-locked loop and the first reference signal is generated by a second phase-locked loop, wherein the first phase-locked loop and the second phase-locked loop use the same reference clock.

14. The device according to claim 1, wherein the transmitted signal is generated by mixing a signal from a first oscillator and a second oscillator, and wherein the first reference signal is generated by the second oscillator.

15. The device according to claim 1, further comprising a vital sign estimator to determine at least one of a heart rate and a respiratory rate by performing a frequency analysis of a signal based on the output signal of the phase or frequency comparator.

16. The device according to claim 1, wherein a frequency of the vital sign carrying signal is tracked.

17. The device according to claim 1, further comprising an integrator so that a phase of the vital sign carrying signal is tracked and the output signal from the phase or frequency comparator is integrated.

18. The device according to claim 17, wherein the integrator estimates a magnitude of tissue motion based on heart or respiratory action of the subject by determining an amplitude of a frequency component of the integrated output.

19. A method of detecting a vital sign comprising at least one of a heart rate and a respiratory rate of a subject, the method comprising:
    transmitting a radio frequency signal towards the subject;
    receiving a reflected signal from the subject, wherein the transmitted signal is reflected by the subject and Doppler-shifted due to at least one of the heart rate and the respiratory rate to form the reflected signal;
    mixing the reflected signal with a first reference signal;
    providing a vital sign carrying signal based on the mixing of the reflected signal with the first reference signal to a first input of a phase or frequency comparator;
    generating an adjustable second reference signal by a reference signal generator and providing the adjustable second reference signal to a second input of the phase or frequency comparator;
    generating an output signal by the phase or frequency comparator based on the vital sign carrying signal and the adjustable second reference signal; and
    varying by the reference signal generator at least one of a phase and a frequency of the adjustable second reference signal based on the output signal of the phase or frequency comparator to track a phase or frequency of the vital sign carrying signal, the method using the device according to claim 1.

* * * * *